(12) United States Patent
Al-Hellani et al.

(10) Patent No.: US 8,492,497 B2
(45) Date of Patent: Jul. 23, 2013

(54) COPOLYMERS, THEIR USE AS THICKENERS, AND METHODS FOR THEIR PREPARATION

(75) Inventors: Rabie Al-Hellani, Ludwigshafen (DE); Bernd Bruchmann, Freinsheim (DE); Daniel Schoenfelder, Brussels (BE); Anna Cristadoro, Heppenheim (DE); Reinhold J Leyrer, Dannstadt-Schauernheim (DE); Cristofer Arisandy, Ilvesheim (DE)

(73) Assignee: BASF SE, Ludwigshafen (DE)

( * ) Notice: Subject to any disclaimer, the term of this patent is extended or adjusted under 35 U.S.C. 154(b) by 314 days.

(21) Appl. No.: 12/834,310

(22) Filed: Jul. 12, 2010

(65) Prior Publication Data

US 2011/0015361 A1    Jan. 20, 2011

(30) Foreign Application Priority Data

Jul. 15, 2009    (EP) .................................... 09165576

(51) Int. Cl.
| | | |
|---|---|---|
| *C08F 20/58* | (2006.01) | |
| *C08F 22/38* | (2006.01) | |
| *C08F 20/06* | (2006.01) | |
| *C08F 22/02* | (2006.01) | |
| *C08F 122/02* | (2006.01) | |
| *C08F 16/12* | (2006.01) | |

(52) U.S. Cl.
USPC ..................... 526/304; 526/318.2; 526/318.5; 526/333

(58) Field of Classification Search
USPC ............................ 526/304, 318.2, 318.5, 333
See application file for complete search history.

(56) References Cited

FOREIGN PATENT DOCUMENTS

| JP | 01313600 A | * | 12/1989 |
| JP | 2000273794 A | * | 10/2000 |
| WO | WO 99/04313 A1 | | 1/1999 |
| WO | WO 99/06524 A1 | | 2/1999 |
| WO | WO 99/65958 A1 | | 12/1999 |

OTHER PUBLICATIONS

"Liquid Detergents", Editor: Kuo-Yann Lai, Surfactant Sci. Ser., vol. 67, Marcel Decker, New York, 1997, pp. 272-304.
U.S. Appl. No. 12/834,373, filed Jul. 12, 2010, Herth, et al.
U.S. Appl. No. 13/028,624, filed Feb. 16, 2011, Roller et al.
U.S. Appl. No. 13/440,463, filed Apr. 5, 2012, Henningsen, et al.

\* cited by examiner

*Primary Examiner* — Karuna P Reddy
(74) *Attorney, Agent, or Firm* — Oblon, Spivak, McClelland, Maier & Neustadt, L.L.P.

(57) ABSTRACT

The present invention relates to copolymers comprising as comonomers in copolymerized form (A) at least one ethylenically unsaturated mono- or dicarboxylic acid,
(B) at least one ethylenically unsaturated compound which has at least one structural unit of the general formula (I) per molecule:

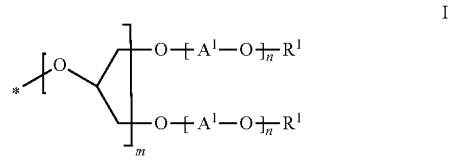

where the variables are defined as follows:

$R^1$ is different or identical and selected from hydrogen, $C_1$-$C_{30}$-alkyl, $C_6$-$C_{30}$-aryl and $C_7$-$C_{30}$-aralkyl, $A^1$ is different or identical and selected from $C_2$-$C_{10}$-alkylene, $C_6$-$C_{10}$-arylene and $C_7$-$C_{10}$-aralkylene, n is different or identical and selected from zero to 200,
m is different or identical and selected from 1 to 6, (C) at least one further comonomer.

14 Claims, No Drawings

COPOLYMERS, THEIR USE AS THICKENERS, AND METHODS FOR THEIR PREPARATION

The present invention relates to copolymers comprising as comonomer in copolymerized form
(A) at least one ethylenically unsaturated mono- or dicarboxylic acid,
(B) at least one (co)polymer which has at least one structural unit of the general formula I per molecule:

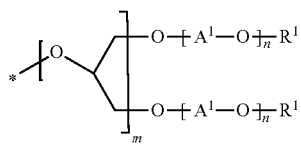

where the variables are defined as follows:
$R^1$ is identical or different and selected from hydrogen, $C_1$-$C_{30}$-alkyl, $C_3$-$C_{10}$-cycloalkyl, $C_6$-$C_{30}$-aryl and $C_7$-$C_{30}$-aralkyl,
$A^1$ is identical or different and selected from $C_2$-$C_{10}$-alkylene, $C_6$-$C_{10}$-arylene and $C_7$-$C_{10}$-aralkylene,
n is identical or different and selected from zero to 200,
m is identical or different and selected from 1 to 6,
(C) at least one further comonomer.

Furthermore, the present invention relates to the use of copolymers according to the invention as thickeners, for example in detergents or cleaners.

Furthermore, the present invention relates to compounds (B) which are particularly suitable as comonomers for preparing copolymers according to the invention.

Furthermore, the present invention relates to compounds which are particularly suitable for the synthesis of (co)polymers according to the invention.

In order to adjust the viscosity in aqueous formulations, for example detergents and cleaners, in printing pastes or in body care compositions and chemical preparations, thickeners are often used. Thickeners may be natural or synthetic thickeners. Known synthetic thickeners are in many cases copolymers of acrylic acid with acrylamide that are neutralized with ammonia and which comprise small amounts of an ethylenically diunsaturated comonomer, such as, for example, methylenebisacrylamide, in copolymerized form.

The properties of known thickeners can also be improved.

Undesired in many cases is the white oil which is required for the synthesis of the thickeners, is thus still present at least proportionally in the synthetic thickeners in question and which remains in applications on fibrous materials such as, for example, textile, where it can lead to impaired fastnesses and to impaired handle. Particularly if the wish is to use printing pastes based on disperse dyes (dispersion dyes) or reactive dyes, it is then desirable to remove the thickener through simple washing, something which is in many cases not possible when using thickeners containing white oil.

Attempts have also been made to remove the white oil following the synthesis of the thickener, for example by drying the thickener, in particular by spray-drying. This then gives so-called powder thickeners, although these cannot always be readily stirred into other formulations.

Attempts have been made to circumvent the disadvantages of white oil by using associative thickeners. Associative thickeners are water-soluble polymers and have surfactant-like hydrophobic constituents which are able to interact, in particular to associate and to form a network, in a hydrophilic, in particular aqueous, medium both with themselves and also with other hydrophobic substances. The resulting associative network leads to the medium becoming thickened or gelatinized.

However, known associative thickeners can still be improved. In particular, the salt stability is still inadequate in many cases. Moreover, in the case of liquid detergents, in many cases improved transparency is desired, which facilitates better sales success.

WO 99/65958 describes alkali-soluble thickeners which comprise the reaction product of an unsaturated carboxylic acid, of a monoethylenically unsaturated monomer and of a hydrophobic, alkoxylated macromonomer. The monoethylenically unsaturated monomer comprises a methyl group; it is preferably methyl acrylate. These polymers should be water-soluble even at a pH in the range from 4.5 to 6.0 and are therefore suitable for cosmetic products.

It was therefore an object to provide detergents which have improved washing behavior at a high salt content and improved transparency. It was also the object to provide additives for detergents with the help of which the desired properties can be established. It was also the object to provide a method of preparing the additives in question.

Accordingly, the copolymers defined at the start have been found, also referred to in short as copolymers according to the invention. Copolymers according to the invention comprise as comonomers in copolymerized form
(A) at least one ethylenically unsaturated mono- or dicarboxylic acid,
(B) at least one (co)polymer, which is described in more detail below and which is also referred to in short as compound (B) or compound (B) according to the invention,
(C) at least one further comonomer.

Suitable ethylenically unsaturated mono- or dicarboxylic acids (A) are, for example, ethylenically mono- and polyunsaturated mono- or dicarboxylic acids, for example sorbic acid, and in particular monoethylenically unsaturated $C_3$-$C_{10}$-monocarboxylic acids, monoethylenically unsaturated $C_4$-$C_{10}$-dicarboxylic acids and their low molecular weight anhydrides. Examples of suitable monoethylenically unsaturated $C_4$-$C_{10}$-dicarboxylic acids and their low molecular weight anhydrides are itaconic acid, citraconic acid, mesaconic acid, glutaconic acid, aconitic acid, maleic acid, fumaric acid, maleic anhydride, itaconic anhydride and mixtures of two or more of the aforementioned compounds. Examples of suitable monoethylenically unsaturated $C_3$-$C_{10}$-monocarboxylic acids are ethacrylic acid, (E)- and (Z)-crotonic acid and preferably acrylic acid. Particular preference is given to methacrylic acid.

In one variant of the present invention, mixtures of a monoethylenically unsaturated $C_3$-$C_{10}$-monocarboxylic acid and of a monoethylenically unsaturated $C_4$-$C_{10}$-dicarboxylic acid or its anhydride, for example of (meth)acrylic acid and maleic anhydride, are used.

Copolymers according to the invention further comprise at least one compound (B) in copolymerized form. Per molecule, compounds (B) have at least one, for example on average 1 to 10 (number-average), preferably up to 5 and particularly preferably up to 2, structural units of the general formula I,

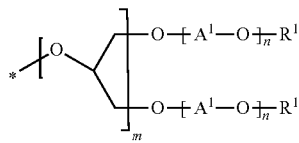

I where the variables are defined as follows:

$R^1$ is different or preferably identical and selected from hydrogen and preferably $C_6$-$C_{30}$-aryl, preferably $C_6$-$C_{14}$-aryl, for example phenyl, 1-naphthyl, 2-naphthyl, 1-anthracenyl, 2-anthracenyl, 9-anthracenyl, $C_7$-$C_{30}$-aralkyl, preferably benzyl, $C_3$-$C_{10}$-cycloalkyl, substituted or unsubstituted, preferably cyclopentyl, cyclohexyl, cyclooctyl, where one or more nonadjacent carbon atoms may be replaced by oxygen or N—H or N—$CH_3$, examples which may be mentioned being 1,3-dioxolanyl, 1,3-dioxanyl or 1,3-oxazolinyl, preferably 2,2-dimethyl-1,3-dioxolanyl and 2,2-dimethyl-1,3-dioxanyl, and in particular $C_1$-$C_{30}$-alkyl, preferably $C_1$-$C_{20}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, n-dodecyl, isododecyl, n-tetradecyl, isotetradecyl, n-hexadecyl, isohexadecyl, n-octadecyl, isooctadecyl, n-eicosyl, isoeicosyl.

$A^1$ is different or preferably identical and selected from $C_6$-$C_{10}$-arylene, for example orthophenylene, metaphenylene, paraphenylene, 1,6-naphthylene, 1,7-naphthylene, 2,6-naphthylene, 2,7-naphthylene or 1,8-naphthylene, $C_7$-$C_{10}$-aralkylene, such as, for example, —CH($C_6H_5$)— or —$CH_2$—CH($C_6H_5$)—, and in particular from $C_2$-$C_{10}$-alkylene, substituted or preferably unsubstituted, for example —$CH_2$—, —CH($CH_3$)—, —CH($C_2H_5$)—, —C($CH_3$)$_2$—, —$CH_2$—$CH_2$—, —CH($CH_3$)—$CH_2$—, —$CH_2$—CH($CH_3$)—, —CH($C_2H_5$)—$CH_2$—, —$CH_2$—CH($C_2H_5$)—, —$(CH_2)_3$—, —$(CH_2)_4$—, —$(CH_2)_5$—, —$(CH_2)_6$—, —$(CH_2)_8$—, —$(CH_2)_{10}$—, preferably —$CH_2$—$CH_2$—, —CH($CH_3$)—$CH_2$—, —$CH_2$—CH($CH_3$)—, very particularly preferably —$CH_2$—$CH_2$—, n is different or identical and selected from zero to 200, preferably 1 to 150, particularly preferably 5 to 50, m is selected from 1 to 6, preferably up to 4, particularly preferably up to 2.

Here, the variable n may be an average value.

Compound (B) may be a homopolymer, which may then also be called polymer (B). However, it is preferably copolymers, called copolymers (B) in short, selected from block copolymers, graft copolymers, alternating copolymers or preferably from random copolymers. Compound (B) can be prepared, for example, by ionic, for example anionic, or preferably by free-radical (co)polymerization of one or more (co)monomers of which at least one has a structural unit of the general formula I.

Structural units of the formula I can, for example, appear as follows:

m = 1:

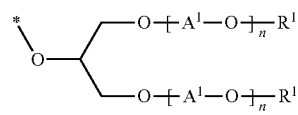

m = 2:

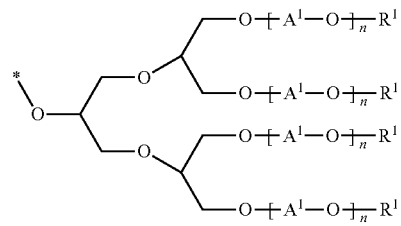

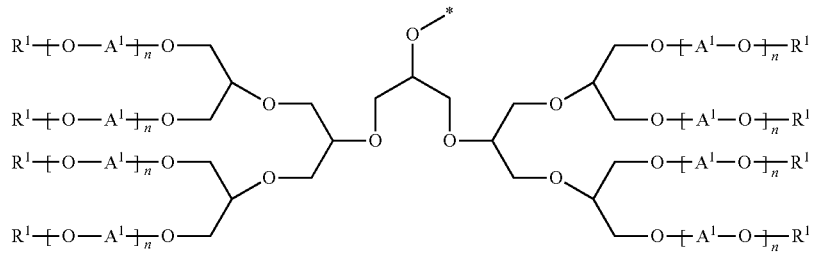

m = 3

In one embodiment of the present invention, compounds (B) are contaminated with products of an incomplete conversion. On account of an incomplete conversion, the following structural units, for example, may then be formed:

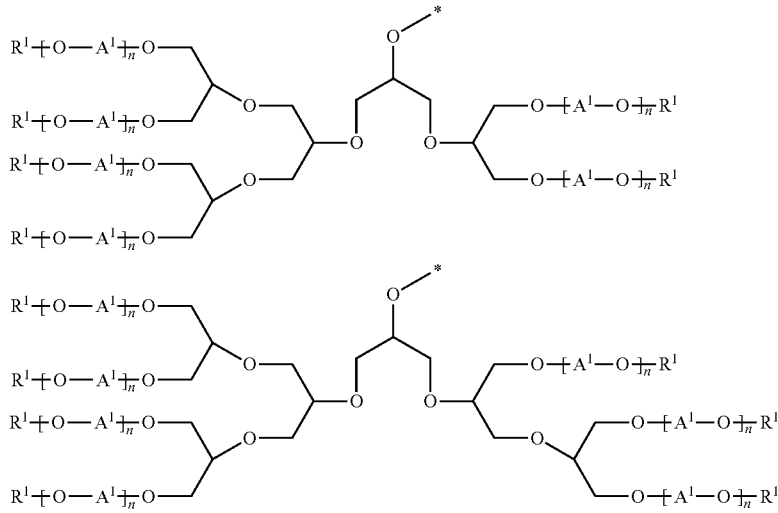

If it is desired to use random copolymers as copolymer, it is possible to use those copolymers which, besides structural units of the general formula I, also have at least one structural unit which can be attributed to the comonomer, where any desired free-radically polymerizable comonomers are suitable, for example vinyl aromatics, in particular styrene, vinyl esters, in particular vinyl acetate, ethylenically unsaturated carboxylic acids, in particular (meth)acrylic acid, amides or esters of ethylenically unsaturated carboxylic acids, in particular $C_1$-$C_{10}$-alkyl esters of (meth)acrylic acid and (meth)acrylonitrile, also maleic anhydride, halogen-containing comonomers, such as, for example, vinyl chloride or vinylidene chloride and α-olefins, for example 1-decene, 1-hexene, isobutene or 1-dodecene.

If it is desired to use random copolymers as copolymer, it is possible to use those copolymers which, besides structural units with the general formula I, have at least one structural unit of the general formula II,

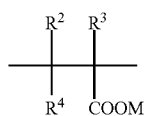

where the variables are defined as follows:
$R^2$, $R^3$ are identical or different and selected from $C_1$-$C_6$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl; preferably n-$C_1$-$C_4$-alkyl, such as methyl, ethyl, n-propyl, isopropyl, n-butyl, isobutyl, sec-butyl and tert-butyl, particularly preferably methyl
and in particular hydrogen,
$R^4$ is $C_1$-$C_6$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, iso-amyl, n-hexyl, isohexyl, sec-hexyl; preferably n-$C_1$-$C_4$-alkyl such as methyl, ethyl, n-propyl, isopropyl, n-butyl, isobutyl, sec-butyl and tert-butyl, particularly preferably methyl
and in particular COOM or hydrogen,
M is selected from ammonium, substituted, such as, for example methylammonium, dimethylammonium, trimethylammonium, ethanolammonium, or preferably unsubstituted, and in particular hydrogen and metal cations, for example alkali metal cations such as $Li^+$, $Na^+$, $K^+$, $Rb^+$ or $Cs^+$, preferably $Na^+$ or $K^+$, M may also be a half equivalent of an alkaline earth metal cation, for example a half equivalent $Ca^{2+}$ or $Mg^{2+}$.

In one embodiment of the present invention, $R^3$ is methyl, and $R^2$ and $R^4$ are in each case hydrogen.

In one embodiment of the present invention, $R^2$, $R^3$ and $R^4$ are in each case hydrogen.

In one embodiment of the present invention, $R^2$ and $R^3$ are in each case hydrogen, and $R^4$ is COOM.

In one embodiment of the present invention, compound (B) has a molecular weight $M_w$ in the range from 200 to 100 000 g/mol, preferably 1000 to 10 000 g/mol, particularly preferably up to 5000 g/mol, determined for example by gel permeation chromatography (GPC).

In one embodiment of the present invention, compound (B) has a K value in accordance with Fikentscher in the range from 8 to 40, measured at 23° C. in THF/water mixtures, preferably in 2% by weight of THF in water.

In one embodiment of the present invention, compound (B) has a polydispersity $M_w/M_n$ in the range from 1 to 4, preferably from 1.1 to 2 and particularly preferably in the range from 1.1 to 1.5.

In one embodiment of the present invention, compound (B) has a hydroxyl number in the range from 1 to 270, preferably 5 to 10, particularly preferably 10 to 70 mg KOH/g, determined in accordance with DIN 53240.

In one embodiment of the present invention, copolymer according to the invention has a molecular weight $M_w$ in the range from 1000 to 10 000 000 g/mol, preferably 10 000 to 1

000 000 g/mol, particularly preferably 50 000 to 500 000 g/mol, determined for example by gel permeation chromatography (GPC).

In one embodiment of the present invention, copolymer according to the invention has a polydispersity $M_w/M_n$ in the range from 1 to 10.

In one embodiment of the present invention, the molar ratio of structural units of the formula I to structural units of the formula II in copolymer according to the invention is in the range from 0.01 to 10, preferably 0.05 to 2 and particularly preferably 0.1 to 0.5.

In one embodiment of the present invention, at least one structural unit of the general formula I is bonded to the basic backbone of copolymer according to the invention via a group of the formula III a

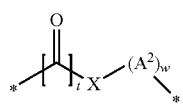

or III b

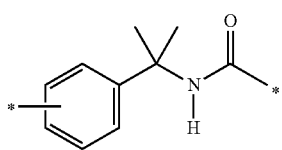

where the variables are selected as follows:
X is selected from a single bond, N—H and preferably oxygen,
t is selected from zero and one,
w is selected from zero and one,
$A^2$ is selected from $C_1$-$C_{50}$-alkylene, substituted or preferably unsubstituted, where one or more nonadjacent $CH_2$ groups may be replaced by oxygen. Examples of suitable groups $A^2$ are $C_2$-$C_{10}$-alkylene, preferably —$CH_2$—$CH_2$—, —$CH(CH_3)$—$CH_2$—, —$CH_2$—$CH(CH_3)$—, particularly preferably —$CH_2$—$CH_2$—, furthermore —$CH_2$—$CH_2$—O—, —$CH(CH_3)$—$CH_2$—O—, —$CH_2$—$CH(CH_3)$—O—, —[$CH_2$—$CH_2$—O—]$_y$—, —[$CH(CH_3)$—$CH_2$—O—]$_y$—, —[$CH_2$—$CH(CH_3)$—O]$_y$—, where y is an integer in the range from 2 to 20, preferably 2 to 15 and in particular 3 to 10.

Copolymers according to the invention furthermore comprise at least one further comonomer (C) in copolymerized form. Suitable comonomers are ethylenically unsaturated compounds which can be copolymerized free-radically with the comonomers (A) and (B). Examples which may be mentioned are: $C_1$-$C_{10}$-alkyl esters of ethylenically unsaturated mono- or dicarboxylic acids, in particular of (meth)acrylic acid, vinyl acetate, vinyl aromatics such as, in particular, styrene and α-methylstyrene, α-olefins such as, in particular, $C_{12}$-$C_{20}$-α-olefins, furthermore vinyl chloride, acrylonitrile and N-vinylpyrrolidone. Preferred examples of $C_1$-$C_{10}$-alkyl esters of ethylenically unsaturated monocarboxylic acids are methyl(meth)acrylate, ethyl(meth)acrylate, n-butyl(meth) acrylate and 2-ethylhexyl(meth)acrylate.

In one embodiment of the present invention, copolymer according to the invention comprises at least two different further comonomers (C) in copolymerized form. In another embodiment of the present invention, copolymer according to the invention comprises precisely one further comonomer (C) in copolymerized form.

In one embodiment of the present invention, copolymer according to the invention comprises in copolymerized form:
0.1 to 99% by weight, preferably 5 to 70% by weight, particularly preferably 10 to 50% by weight, of ethylenically unsaturated mono- or dicarboxylic acid (A),
0.001 to 99% by weight, preferably 0.01 to 50% by weight, particularly preferably 0.1 to 10% by weight, of compound (B),
in total 0.1 to 99% by weight, preferably 5 to 80% by weight, particularly preferably 30 to 60% by weight, of further comonomer(s) (C).

Here, data in % by weight are in each case based on the total copolymer according to the invention.

The present invention further provides the use of copolymers according to the invention as thickeners, in particular as associative thickeners. In this connection, copolymers according to the invention utilize their property that they have a strongly pH-dependent solubility behavior in aqueous medium. A further aspect of the present invention is accordingly the use of the copolymers according to the invention as additive in detergents and cleaners and also in cosmetic preparations. Also provided is a method of cleaning textile substrates using the copolymers according to the invention.

The present invention further provides detergents and cleaners and also cosmetic preparations comprising at least one copolymer according to the invention. In this connection, detergents are to be understood primarily as meaning detergents for textile, whereas cleaners refer to hard surfaces such as, for example, porcelain, ceramic, glass, stone, wood or concrete. Cosmetic preparations are to be understood as meaning not only ointments, lotions, peels and other preparations which are directly suitable as cosmetic preparations, but also those preparations which are used as a basis for cosmetic consumer products.

In this connection, copolymers according to the invention can be used in the form of the free acids or in partially or completely neutralized form, for example partially or completely neutralized with ammonium, alkaline earth metal or preferably alkali metal cations. Preferably, copolymers according to the invention are used in unneutralized form, i.e. as the free acid, and neutralization is only carried out directly before or during the washing or cleaning operation.

Detergents and cleaners according to the invention or cosmetic preparations according to the invention may be present in liquid or solid form.

Solid detergents according to the invention preferably comprise the following components:
(a) 0.05 to 20% by weight of at least one copolymer according to the invention,
(b) 0.5 to 40% by weight of at least one nonionic, anionic and/or cationic surfactant,
(c) 0.5 to 50% by weight of an organic builder,
(d) 0 to 10% by weight of an organic cobuilder and
(e) 0 to 60% by weight of other customary ingredients, such as extenders, enzymes, perfume, complexing agents, corrosion inhibitors, bleaches, bleach activators, bleach catalysts, color transfer inhibitors, further graying inhibitors, soil release polyesters, fiber and color protection additives, silicones, dyes, bactericides, dissolution improvers and/or disintegrants,
where the sum of the components (a) to (e) is preferably 100% by weight.

Solid detergent formulations according to the invention may be present in powder, granule, extrudate or tablet form.

Liquid detergent formulations according to the invention preferably have the following composition:
(a) 0.05 to 20% by weight of at least one copolymer according to the invention,
(b) 0.5 to 40% by weight of at least one nonionic, anionic and/or cationic surfactant,
(c) 0 to 20% by weight of an inorganic builder,
(d) 0 to 10% by weight of an organic cobuilder,
(e) 0 to 60% by weight of other customary ingredients, such as sodium carbonate, enzymes, perfume, complexing agents, corrosion inhibitors, bleaches, bleach activators, bleach catalysts, color transfer inhibitors, further graying inhibitors, soil release polyesters, fiber and color protection additives, silicones, dyes, bactericides, organic solvents, solubility promoters, hydrotropes, thickeners and/or alkanolamines and
(f) 0 to 99.45% by weight of water.

Suitable nonionic surfactants (b) here are primarily:

Alkoxylated $C_8$-$C_{22}$-alcohols, such as fatty alcohol alkoxylates, oxo alcohol alkoxylates and guerbet alcohol alkoxylates: the alkoxylation can take place with $C_2$-$C_{20}$-alkylene oxides, preferably with ethylene oxide, propylene oxide and/or butylene oxide. Block copolymers or random copolymers may be present. Per mol of alcohol, they usually comprise 1 to 50 mol, preferably 1 to 20 mol, of at least one alkylene oxide. A particularly preferred alkylene oxide is ethylene oxide. The alcohols preferably have 10 to 18 carbon atoms.

Alkylphenol alkoxylates, in particular alkylphenol ethoxylates, which comprise $C_6$-$C_{14}$-alkyl chains and 5 to 30 mol of alkylene oxide/mol.

Alkyl polyglucosides which comprise $C_8$-$C_{22}$-, preferably $C_{10}$-$C_{18}$-alkyl chains and usually 1 to 20, preferably 1.1 to 5 glucoside units.

N-alkyl glucamides, fatty acid amide alkoxylates, fatty acid alkanolamide alkoxylates and block copolymers of ethylene oxide, propylene oxide and/or butylene oxide.

Suitable anionic surfactants are, for example:

Sulfates of (fatty) alcohols having 8 to 22, preferably 10 to 18, carbon atoms, in particular $C_9$-$C_{11}$-alcohol sulfates, $C_{12}$-$C_{14}$-alcohol sulfates, $C_{12}$-$C_{18}$-alcohol sulfates, lauryl sulfate, cetyl sulfate, myristyl sulfate, palmityl sulfate, stearyl sulfate and tallow fatty alcohol sulfate.

Sulfated alkoxylated $C_8$-$C_{22}$-alcohols (alkyl ether sulfates): compounds of this type are prepared, for example, by firstly alkoxylating a $C_8$-$C_{22}$-, preferably a $C_{10}$-$C_{18}$-alcohol, e.g. a fatty alcohol, and then sulfating the alkoxylation product. For the alkoxylation, ethylene oxide is preferably used.

Linear $C_8$-$C_{20}$-alkylbenzenesulfonates (LAS), preferably linear $C_9$-$C_{13}$-alkylbenzenesulfonates and -alkyltoluenesulfonates.

Alkanesulfonates, in particular $C_8$-$C_{24}$-, preferably $C_{10}$-$C_{18}$-alkansulfonates.

Soaps, such as the Na and K salts of $C_8$-$C_{24}$-carboxylic acids.

An anionic surfactant is added to the detergent preferably in the form of salts. Suitable cations here are, for example, alkali metal ions, such as sodium, potassium and lithium, and ammonium salts, such as hydroxyethylammonium, di(hydroxyethyl)ammonium and tri(hydroxyethyl)ammonium salts.

Particularly suitable cationic surfactants which may be mentioned are:
$C_7$-$C_{25}$-alkylamines;
N,N-dimethyl-N-(hydroxy-$C_7$-$C_{25}$-alkyl)ammonium salts;
mono- and di-($C_7$-$C_{25}$-alkyl)dimethylammonium compounds quaternized with alkylating agents;
ester quats, in particular quaternary esterified mono-, di- and trialkanolamines which have been esterified with $C_8$-$C_{22}$-carboxylic acids;
imidazoline quats, in particular 1-alkylimidazolinium salts of the formulae VI or VII

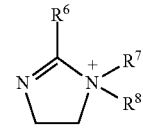

VI

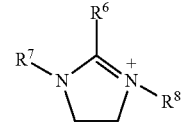

VII in which the variables have the following meaning:
$R^6$ is identical or different and selected from $C_1$-$C_{25}$-alkyl or $C_2$-$C_{25}$-alkenyl;
$R^7$ is $C_1$-$C_4$-alkyl or hydroxy-$C_1$-$C_4$-alkyl;
$R^8$ is $C_1$-$C_4$-alkyl, hydroxy-$C_1$-$C_4$-alkyl or a radical $R^6$—(CO)—Y—$(CH_2)_p$— (Y is oxygen or —NH—; p: 2 or 3),
where if $R^8$ is $R^6$—(CO)—Y—$(CH_2)_p$—, at least one radical $R^6$ is $C_7$-$C_{22}$-alkyl.

Suitable inorganic builders are in particular:

Crystalline and amorphous alumosilicates with ion-exchanging properties, such as primarily zeolites: various types of zeolites are suitable, in particular the zeolites A, X, B, P, MAP and HS in their Na form or in forms in which Na is partially exchanged for other cations such as Li, K, Ca, Mg or ammonium, Crystalline silicates, such as in particular disilicates and sheet silicates, e.g. δ- and -β-$Na_2SiO_2O_5$. The silicates can be used in the form of their alkali metal salts, alkaline earth metal salts or ammonium salts, preference being given to the Na, Li and Mg silicates, Amorphous silicates, such as sodium metasilicate and amorphous disilicate, Carbonates and hydrogencarbonates: these can be used in the form of their alkali metal salts, alkaline earth metal salts or ammonium salts. Preference is given to Na, Li and Mg carbonates and hydrogencarbonates, in particular sodium carbonate and/or sodium hydrogencarbonate, Polyphosphates, such as pentasodium triphosphate.

Suitable organic cobuilders are primarily:

Low molecular weight carboxylic acids, such as citric acid, hydrophobically modified citric acid, e.g. agaric acid, malic acid, tartaric acid, gluconic acid, glutaric acid, succinic acid, imidodisuccinic acid, oxydisuccinic acid, propane tricarboxylic acid, butantetracarboxylic acid, cyclopentanetetracarboxylic acid, alkyl- and alkenylsuccinic acids and aminopolycarboxylic acids, e.g. nitrilotriacetic acid, β-alaninediacetic acid, ethylendiamintetraacetic acid, serinediacetic acid, isoserinediacetic acid, N-(2-hydroxyethyl)iminodiacetic acid, ethylendiaminodisuccinic acid and methyl- and ethylglycinediacetic acid.

Oligomeric and polymeric carboxylic acids, such as homopolymers of acrylic acid and aspartic acid, oligomaleic acids, copolymers of maleic acid with acrylic acid, methacrylic acid or $C_2$-$C_{22}$-olefins, e.g. isobutene or long-chain α-olefins, with vinyl $C_1$-$C_8$-alkyl ethers, vinyl acetate, vinyl propionate, (meth)acrylic acid esters of $C_1$-$C_8$-alcohols and/or styrene, copolymers of acrylic acid with methacrylic acid or $C_2$-$C_{22}$-olefins, e.g. isobutene or long-chain α-olefins, in particular with $C_{10}$-$C_{22}$-α-olefins, vinyl $C_1$-$C_8$-alkyl ethers, vinyl acetate, vinyl propionate, (meth)acrylic acid esters of $C_1$-$C_8$-alcohols and styrene. Preference is given to the homopolymers of acrylic acid and copolymers of acrylic acid with maleic acid. Oligomeric and polymeric carboxylic acids are used in acid form or as sodium salt.

Suitable bleaches are, for example, adducts of hydrogen peroxide onto inorganic salts, such as sodium perborate monohydrate, sodium perborate tetrahydrate and sodium carbonate perhydrate, and percarboxylic acids, such as phthalimidopercaproic acid.

Suitable bleach activators are, for example, N,N,N',N'-tetraacetylethylenediamine (TAED), sodium p-nonanoyloxybenzenesulfonate and N-methylmorpholinium acetonitrile methylsulfate.

Enzymes preferably used in detergents are proteases, lipases, amylases, cellulases, oxidases and peroxidases.

Suitable color transfer inhibitors are, for example, homopolymers, copolymers and graft polymers of 1-vinylpyrrolidone, 1-vinylimidazole or 4-vinylpyridine N-oxide. Homopolymers and copolymers of 4-vinylpyridine reacted with chloroacetic acid are also suitable as color transfer inhibitors.

Further detergent ingredients customary per se are known. Detailed descriptions can be found, for example, in WO 99/06524 and WO 99/04313 and in "Liquid Detergents", Editor: Kuo-Yann Lai, Surfactant Sci. Ser., Vol. 67, Marcel Decker, New York, 1997, page 272-304.

Moreover, it has been found that copolymers according to the invention and aqueous dispersions or solutions of copolymer according to the invention can be used as thickeners in cleaners for hard surfaces. The present invention therefore provides the use of copolymers according to the invention and of aqueous dispersions or solutions of copolymer according to the invention as additive for cleaners for hard surfaces. The present invention further provides cleaners for hard surfaces, comprising copolymer according to the invention. The present invention further provides a method of cleaning hard surfaces using copolymer according to the invention or aqueous dispersions or solutions of copolymer according to the invention.

Cleaners for hard surfaces are to be understood as meaning, for example, cleaners for the cleaning of metal, plastic, glass and ceramic, floor cleaners, sanitary cleaners, all-purpose cleaners in the home and in commercial applications, industrial cleaners (for use in car-washing plants or high-pressure cleaners), low-temperature cleaners, dishwashing cleaners, rinse aids, disinfectant cleaners, cleaners for the food and beverage industry, in particular as bottle cleaners, as CIP cleaners (Cleaning-in-Place) in dairies, breweries and other operations of food manufacturers. Cleaners which comprise copolymer according to the invention are suitable particularly for the cleaning of hard surfaces such as glass, plastic and metal. The cleaners can be rendered alkaline, acidic or neutral. They usually comprise one or more surfactants in amounts of from about 0.2 to 50% by weight. These may be anionic, nonanionic or cationic surfactants and also mixtures of surfactants which are compatible with one another, e.g. mixtures of anionic and nonionic or of cationic and nonionic surfactants. Alkaline cleaners can comprise sodium carbonate, potassium carbonate, sodium hydrogen carbonate, potassium hydrogen carbonate, sodium sesquicarbonate, potassium sesquicarbonate, sodium hydroxide, potassium hydroxide, amine bases such as monoethanolamine, diethanolamine, triethanolamine, ammonia or silicate in amounts up to 60% by weight, in some cases even up to 80% by weight. Cleaners according to the invention for hard surfaces can, moreover, comprise citrates, gluconates or tartrates in amounts up to 80% by weight. Cleaners according to the invention for hard surfaces may be in solid or liquid form.

In one embodiment of the present invention, copolymer according to the invention is present in cleaners according to the invention for hard surfaces in amounts of from 0.1 to 20, preferably 0.2 to 15% by weight.

The present invention further provides cosmetic preparations comprising at least one copolymer according to the invention. Cosmetic preparations according to the invention can be used, for example, for the care of skin, hair, horny skin, fingernails or toenails or for oral care.

Cosmetic preparations according to the invention can be in the form of aqueous or aqueous-alcoholic solutions, or in the form of O/W or W/O emulsions.

In one embodiment of the present invention, cosmetic preparations according to the invention are in the form of shampoos, creams, foams, sprays (pump spray or aerosol), gels, gel sprays, lotions or mousse and can accordingly be formulated with customary further auxiliaries.

The cosmetic preparations according to the invention may be skin cosmetic, hair cosmetic, pharmaceutical, hygiene or pharmaceutical compositions. On account of their film-forming properties, the copolymers described above are suitable in particular as additives for hair cosmetics and skin cosmetics.

Cosmetic preparations according to the invention are preferably in the form of a spray, a gel, a foam, an ointment, cream, an emulsion, a suspension, a lotion, a milk or a paste. If desired, liposomes or microspheres can also be used.

Besides copolymer according to the invention, cosmetic preparations according to the invention can comprise at least one carrier. Examples of suitable carriers are:
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with mono-, di- or trihydric alcohols that are different from iii),
v) saturated acyclic and cyclic hydrocarbons,
vi) fatty acids,
vii) fatty alcohols,
viii) propellant gases,
and mixtures thereof.

Examples of carriers are, in particular, oils and fats selected from hydrocarbons of low polarity, such as mineral oils; linear saturated hydrocarbons, preferably having more than 8 carbon atoms, such as tetradecane, hexadecane, octadecane etc., cyclic hydrocarbons, such as decahydronaphthalene, branched hydrocarbons; animal and vegetable oils, waxes, wax esters, vaseline, esters, preferably esters of fatty acids, such as, for example the esters of $C_1$-$C_{40}$-monoalkanols with $C_1$-$C_{22}$-monocarboxylic acids, such as isopropyl isostearate, n-propyl myristate, iso-propyl myristate, n-propyl palmitate, isopropyl palmitate, hexacosanyl palmitate, octacosanyl palmitate, triacontanyl palmitate, dotriacontanyl palmitate, tetratriacontanyl palmitate, hexanecosanyl stearate, octacosanyl stearate, triacontanyl stearate, dotriacontanyl stearate, tetratriacontanyl stearate, salicylates, such as $C_1$-$C_{10}$-salicylates, e.g. octyl salicylate, benzoate esters such as $C_{10}$-$C_{15}$-alkyl benzoates, benzyl benzoate, other cosmetic esters, such as fatty acid triglycerides, propylene glycol monolaurate, polyethylene glycol monolaurate, $C_{10}$-$C_{15}$-alkyl lactates and mixtures thereof.

Silicone oils suitable as carriers are, for example, linear polydimethylsiloxanes, poly(methyl-phenylsiloxanes), cyclic siloxanes and mixtures thereof. The number-average molecular weight of the polydimethylsiloxanes and poly(m-ethylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

Oil and fat components preferred as carriers are selected from paraffin and paraffin oils, vaseline, natural fats and oils, such as castor oil, soybean oil, peanut oil, olive oil, sunflower oil, sesame oil, avocado oil, cocoa butter, almond oil, peach kernel oil, castor oil, cod-liver oil, pig grease, spermaceti, spermaceti oil, sperm oil, wheat germ oil, macadamia nut oil, evening primrose oil, jojoba oil, fatty alcohols such as lauryl alcohol, myristyl alcohol, cetyl alcohol, stearyl alcohol, oleyl alcohol, cetyl alcohol, fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candelilla wax, spermaceti, and mixtures of the aforementioned oil and fat components.

Besides copolymer and carrier according to the invention, cosmetic preparations according to the invention can comprise: at least one constituent different from carrier and copolymer according to the invention which is selected from cosmetically effective care substances and active ingredients such as AHA acids, fruit acids, ceramides, phytantriol, collagen, vitamins and provitamins, for example vitamin A, E and C, retinol, bisabolol, panthenol, emulsifiers and coemulsifiers, surfactants, preservatives, perfume oils, hair polymers, hair and skin conditioners, graft polymers, silicone compounds, water-soluble or dispersible silicone-containing polymers, natural and synthetic photoprotective agents, bleaches, gel formers, care agents, colorants, dies, pigments, micropigments such as titanium oxide or zinc oxide, opacifiers, tinting agents, tanning agents, consistency regulators, humectants, refatting agents, collagen, protein hydrolyzates, lipids, antioxidants, antifoams, antistats, emollients, solubility promoters, repellants, superfatting agents, pearlescent waxes, consistency regulators, solubilizers, complexing agents, pH regulators, reflectors, proteins and protein hydrolyzates (e.g. wheat, almond or pea proteins) and softeners.

The present invention further provides compounds (B). Per molecule, compounds (B) according to the invention have at least one structural unit of the general formula I,

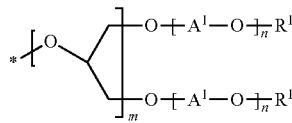

Here, the variables are as defined above:
$R^1$ is different or preferably identical and selected from hydrogen or preferably $C_6$-$C_{30}$-aryl, preferably $C_6$-$C_{14}$-aryl, in particular phenyl; $C_7$-$C_{30}$-aralkyl, preferably benzyl; $C_3$-$C_{10}$-cycloalkyl, in particular cyclopentyl or cyclohexyl, and in particular $C_1$-$C_{30}$-alkyl, preferably $C_1$-$C_{20}$-alkyl.
$A^1$ is different or preferably identical and selected from $C_6$-$C_{10}$-arylene, preferably phenylene, $C_7$-$C_{10}$-aralkylene, such as, for example —CH($C_6H_5$)— or —CH$_2$—CH($C_6H_5$)—, and in particular from $C_2$-$C_{10}$-alkylene, substituted or preferably unsubstituted, preferably —CH$_2$—CH$_2$—, —CH(CH$_3$)—CH$_2$—, —CH$_2$—CH(CH$_3$)—, very particularly preferably —CH$_2$—CH$_2$—,
n is different or identical and selected from zero to 200, preferably 1 to 150, particularly preferably 5 to 50,
m is selected from 1 to 6, preferably to 4, particularly preferably to 2.

In one embodiment of the present invention, compound (B) according to the invention has a molecular weight $M_w$ in the range from 200 to 100 000 g/mol, preferably to 10 000 g/mol, particularly preferably to 5000 g/mol, determined, for example, by gel permeation chromatography (GPC). A suitable standard is, for example, polymethyl methacrylate (PMMA).

In one embodiment of the present invention, compound (B) has a K value in accordance with Fikentscher in the range from 8 to 40, measured at 23° C. in THF/water mixtures, preferably in 2% by weight solution in THF.

In one embodiment of the present invention, compound (B) according to the invention has a polydispersity $M_n/M_w$ in the range from 1 to 4, preferably from 1.1 to 2 and particularly preferably in the range from 1.1 to 1.5.

In one embodiment of the present invention, at least one structural unit of the general formula I is bonded to the basic backbone of copolymer according to the invention via a group of the formula III a

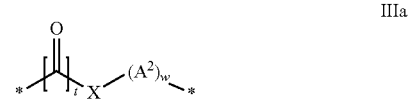

or III b

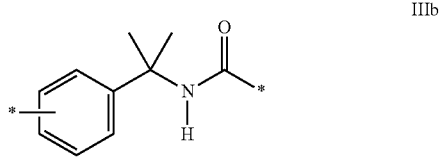

In one embodiment of the present invention, compound (B) according to the invention comprises at least one comonomer of the general formula IV a or IV b in copolymerized form,

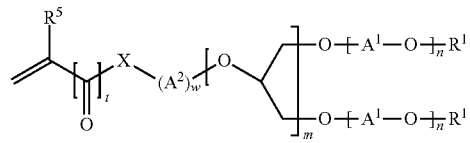

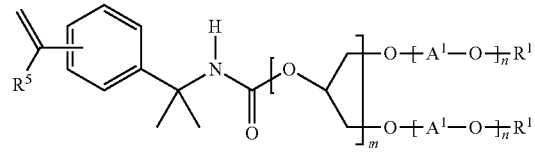

where $R^5$ is selected from methyl and hydrogen and the other variables are as defined above.

The present invention further provides a method of preparing compounds (B) according to the invention wherein at least one (co)monomer of the general formula IV a or IV b

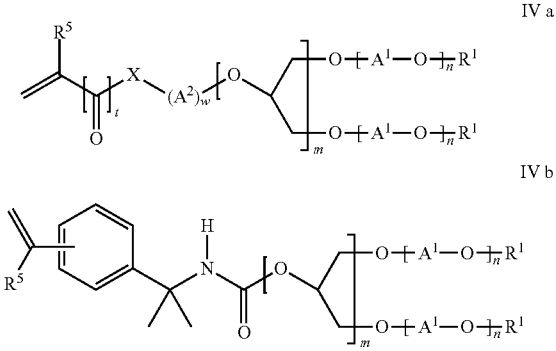

is preferably free-radically polymerized, preferably in the presence of at least one comonomer of the general formula V a to V c

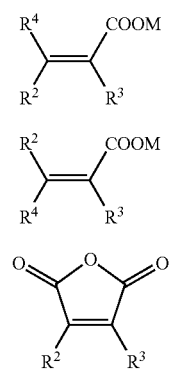

where the variables are defined as follows:
- $R^2$, $R^3$ are identical or different and selected from $C_1$-$C_6$-alkyl, preferably n-$C_1$-$C_4$-alkyl, particularly preferably methyl and in particular hydrogen,
- $R^4$ is $C_1$-$C_6$-alkyl, preferably n-$C_1$-$C_4$-alkyl, particularly preferably methyl, preferably COOM and in particular hydrogen,
- M is selected from ammonium, substituted or preferably unsubstituted, hydrogen and metal cations, in particular alkali metal cations or a half equivalent or alkaline earth metal cations,
- $R^5$ is selected from hydrogen and methyl,
- t is selected from zero and one,
- w is selected from zero and one,
- $A^2$ is selected from $C_1$-$C_{50}$-alkylene, substituted or preferably unsubstituted, where one or more nonadjacent $CH_2$ groups may be replaced by oxygen. Examples of suitable groups $A^2$ are $C_2$-$C_{10}$-alkylene, preferably —$CH_2$—$CH_2$—, —$CH(CH_3)$—$CH_2$—, —$CH_2$—$CH(CH_3)$—, particularly preferably —$CH_2$—$CH_2$—, furthermore —$CH_2$—$CH_2$—O—, —$CH(CH_3)$—$CH_2$—O—, —$CH_2$—$CH(CH_3)$—O—, —[$CH_2$—$CH_2$—O]—, —[$CH(CH_3)$—$CH_2$—O]$_y$—, —[$CH_2$—$CH(CH_3)$—O—]$_y$, where y is an integer in the range from 2 to 20, preferably 2 to 15 and in particular 3 to 10.

For example, compounds (B) according to the invention can be prepared as follows.

Firstly, a compound of the general formula VI a is prepared,

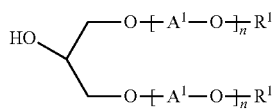

in which the variables are as described above and in which m=1 is selected. For this, at least one compound of the general formula $R^1$—(O-$A^1$)$_n$—OH is reacted with glycerol or preferably a reactive derivative of glycerol, in particular with epichlorohydrin. Here, a molar ratio of compound of the general formula $R^1$—(O-$A^1$)$_n$—OH to reactive derivative of glycerol, in particular epichlorohydrin, is preferably chosen as 2:1. If it is desired to prepare compounds (B) which have structural units of the general formula I, but in which m>1, then further glycerol or further reactive derivative of glycerol is used. This gives those compounds of the general formula VI,

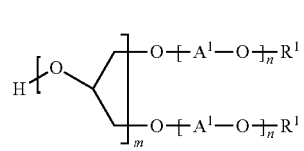

in which m>1. The preparation of compound of the general formula VI or VI a can be carried out, for example, at temperatures in the range from 100 to 110° C. The preparation of compound of the general formula VI a can also be carried out at temperatures below 100° C. The higher the value of m desired in compound of the general formula VI, the higher the temperatures advantageously, for example up to 120° C.

The preparation of compound of the general formula VI or VI a can be carried out in the presence of a catalyst. Suitable catalysts are, for example, inorganic and organic bases. If epichlorohydrin is used as reactive glycerol derivative, then base serves not only as catalyst, but also for neutralizing the HCl which is formed. Suitable inorganic bases are, for example alkali metal carbonates and in particular alkali metal hydroxides, such as NaOH and KOH. Suitable organic bases are, for example, tertiary amines, in particular triethylamine and [2,2,2]diazabicyclooctane (DABCO), and pyridine and para-N,N-dimethylaminopyridine.

In one embodiment of the present invention, the preparation of the compound of the general formula VI or VIa can be carried out in a solvent. Suitable solvents are, for example, ethers, in particular 1,4-dioxane, diisopropyl ether, tetrahydrofuran ("THF") and Di-n-butyl ether. Further suitable solvents are n-butyl acetate ("butyl acetate"), DMSO, N,N-dimethylformamide ("DMF") and N-methylpyrrolidone and aromatic solvents such as, for example, toluene.

In embodiments in which water is eliminated during the preparation of compound of the general formula VI, it is possible to use water-withdrawing agents, for example molecular sieve, sodium sulfate, magnesium sulfate, or the water formed can be removed by azeotropic distillation.

In one embodiment of the present invention, the conversion to compound of the general formula VI is carried out over a period of from 15 minutes to 48 hours, preferably 1 to 24 hours, particularly preferably 3 to 15 hours.

In one embodiment of the present invention, the conversion to compound of the general formula VI is carried out stepwise and in as many stages as corresponds to the desired m. Here, reactive derivate of glycerol, in particular epichlorohydrin, is added in the number of stages in question. For the stepwise reaction, the procedure may involve, for example, firstly reacting a certain amount of compound of the general formula $R^1$—(O-$A^1$)$_n$—OH with half of the number of moles of glycerol or preferably with a reactive derivative of glycerol, in particular with epichlorohydrin. An amount of glycerol or of reactive derivative of glycerol is then added which corresponds to a quarter of the number of moles of compound of the general formula $R^1$—$(O-A^1)_n$—OH, and reacted. If it is desired to carry out a further stage, then an amount of glycerol or of reactive derivative of glycerol is then added which corresponds to one eighth of the number of moles of compound of the general formula $R^1$—$(O-A^1)_n$—OH, and reacted. In each further stage, the number of moles of compound of the general formula $R^1$—$(O-A^1)_n$—OH added is reduced accordingly.

In a further step, compound of the general formula VI can be reacted with a compound with an ethylenic double bond.

For example, compound of the general formula VI can be reacted with a sufficiently reactive derivative of an ethylenically unsaturated carboxylic acid or an ethylenically unsaturated dicarboxylic acid, for example with acid chloride or acid anhydride, in particular with (meth)acrylic anhydride, to give compound according to the invention of the formula IV a, in which t=1 and the other variables are as defined above.

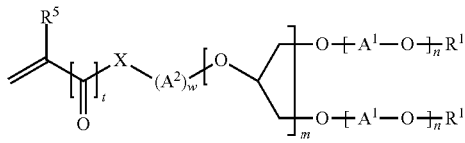

IV a

In one embodiment of the present invention, the reaction of compound of the general formula VI to compound of the general formula IV is carried out at temperatures in the range from −20 to +70° C., preferably from +15 to 50° C.

In one embodiment of the present invention, the reaction of compound of the general formula VI to compound of the general formula IV is carried out in a solvent or a mixture of solvents. Suitable solvents are, for example, ethers, in particular tetrahydrofuran, diethyl ether, 1,4-dioxane, acetone, or nonpolar solvent such as, for example, N,N-dimethylformamide ("DMF"), dimethyl sulfoxide (DMSO) or hydrocarbons, for example cyclohexane.

In one embodiment of the present invention, the reaction of compound of the general formula VI to compound of the general formula IV is carried out in the presence of catalyst. Suitable catalysts are, for example, bases, for example sodium hydride and in particular tertiary amines such as, for example, N,N-dimethylaminopyridine. Catalysts are generally used in substoichiometric amounts. However, if it is desired to use an acid halide as reactive acid derivative, then it is possible to work with an excess of base, in which case the base simultaneously neutralizes the acid formed and can serve as catalyst.

In one embodiment of the present invention, the reaction of compound of the general formula VI to compound of the general formula IV is carried out over a period of from 15 minutes to 12 hours, preferably 1 to 5 hours.

In another embodiment of the present invention, compound of the general formula VI can be reacted with acetylene to give compound according to the invention of the formula IV a, in which t=zero and the other variables are as defined above.

For the reaction with acetylene, it is possible to use one or more catalysts, preferably selected from basic catalysts. KOH is particularly suitable.

The reaction with acetylene can be carried out with or without solvent. Suitable solvents are, for example, N-methylpyrrolidone, N-ethylpyrrolidone, toluene, xylene, THF and dioxane.

The reaction with acetylene can be carried out, for example, at temperatures in the range from 80 to 160° C., preference being given to temperatures around 120° C., for example 110 to 130° C.

The reaction with acetylene can be carried out at atmospheric pressure or preferably at increased pressure, for example at 2 to 30 bar.

In one embodiment of the present invention, the reaction with acetylene is carried out over a period of from 15 minutes to 48 hours, preferably up to 36 hours.

In another embodiment of the present invention, compound of the general formula VI can be reacted with a diisocyanate, for example TMXDI (tetramethylxylylene diisocyanate) to give compound according to the invention of the general formula IV b in which the variables are as defined above.

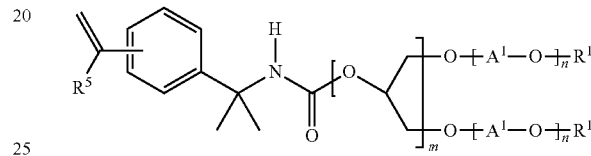

IV b

In one embodiment of the present invention, the preparation of compounds according to the invention of the formula IV b can be carried out in the presence of a catalyst, for example in the presence of an organotin compound, in particular in the presence of DBTL (di-n-butyltin dilaurate).

In one embodiment of the present invention, the preparation of compounds according to the invention of the formula IV b can be carried out in the presence of a solvent. Of suitability are, for example, cyclic and noncyclic ethers, for example THF, 1,4-dioxane and Di-n-butyl ether, also acetone and nonpolar solvents, for example cyclohexane.

In one embodiment of the present invention, the preparation of compounds according to the invention of the formula IV b can be prepared at a temperature in the range from 20 to 100° C., preferably 20 to 80° C.

In one embodiment of the present invention, the preparation of compounds according to the invention of the formula IVb can be prepared over a reaction time in the range from 1 to 10 hours, preferably 2 to 5 hours.

If the desire is to prepare those compounds according to the invention in which $R^1$ is hydrogen, then it is preferred to initially introduce a protective group as $R^1$, for example an acetate protective group, which is cleaved off in a subsequent reaction step, for example under acidic aqueous conditions.

Other preferred protective groups are acetal and ketal protective groups, for example

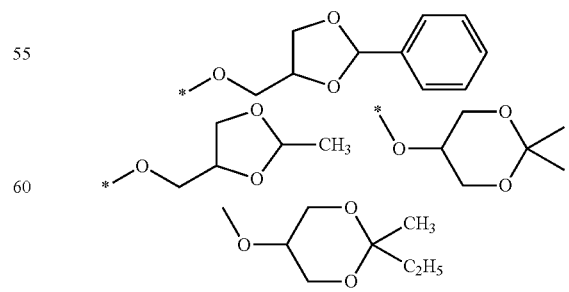

If it is desired to build up a compound according to the invention of the general formula IV on the basis of an acetal or ketal protective group, then the starting material is preferably an acetylated or ketalyted triol, for example acetylated or ketalated glycerol or acetylated or ketalated trimethylolpropane. Reaction is carried out one or more times with epichlorohydrin under the conditions described above to give a branched molecule which can be reacted with, for example, acid chloride or acid anhydride or another suitable derivative of an ethylenically unsaturated carboxylic acid to give compound of the general formula IV a, or with a suitable diisocyanate to give compound of the general formula IV b. By means of hydrolysis under weakly acidic conditions it is possible to cleave off the acetal group or ketal group, if desired, to give compounds according to the invention where $R^1$=hydrogen.

A particularly preferred ketal protective group is the isopropylidene protective group.

It is of course possible to carry out one or more purification operations after each of the aforementioned process steps. Thus, it is, for example, preferred to separate off halides that are formed, for example by filtration. Furthermore, it is preferred to dry out under reduced pressure, for example in order to separate off volatile impurities.

The provisional invention further provides a method of preparing copolymers according to the invention.

The preparation according to the invention of copolymers according to the invention can, for example, be carried out by triggering a preferably free-radical copolymerization of compound of the general formula IV a and/or IV b and comonomer (A) and comonomer(s) (C) with a suitable initiator, if appropriate in the presence of at least comonomer of the general formula V a to V c,

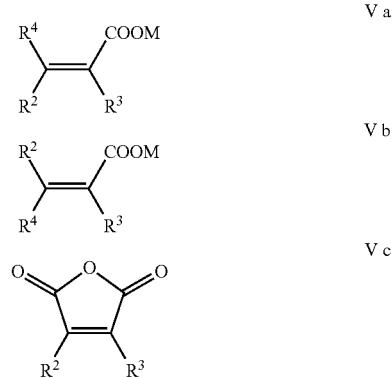

where the variables are defined as follows:
$R^2$, $R^3$ are identical or different and selected from $C_1$-$C_6$-alkyl, preferably n-$C_1$-$C_4$-alkyl, particularly preferably methyl and in particular hydrogen,
$R^4$ is $C_1$-$C_6$-alkyl, preferably n-$C_1$-$C_4$-alkyl, particularly preferably methyl, preferably COOM and in particular hydrogen,
M is selected from ammonium, substituted or preferably unsubstituted, hydrogen and metal cations, in particular alkali metal cations or a half equivalent of alkaline earth metal cations.

Suitable initiators are in particular free-radical initiators, for example organic peroxides, in particular organic peroxides with at least one tert-butyl group or at least one tert-amyl group, and azo compounds, for example azobisisobutyronitrile (AIBN). Also suitable are redox initiators, for example combinations of hydrogen peroxide or sodium peroxodisulfate or one of the aforementioned peroxides with a reducing agent. Suitable reducing agents are, for example: ascorbic acid, tartaric acid, sodium bisulfite, potassium bisulfite, Fe(II) salts, such as, for example, $FeSO_4$ or alkali metal salts of chelates of Fe(II). Furthermore, inorganic peroxides are suitable, for example potassium peroxodisulfate and sodium peroxodisulfate.

The preparation according to the invention of copolymers according to the invention by copolymerization of compound of the general formula IV a and/or IV b, within the context of the present invention also termed copolymerization according to the invention, can be carried out, for example, using at least one solvent. Suitable solvents may be, for example: N,N-dimethylformamide (DMF), dioxane, toluene or nonpolar solvents such as, for example, cyclohexane.

In one embodiment of the present invention, water is a suitable solvent. This is particularly the case when it is desired to initiate the copolymerization according to the invention with inorganic peroxide.

In another embodiment of the present invention, the copolymerization according to the invention is carried out without use of a solvent.

In one embodiment of the present invention, a range from 60 to 95% by weight, preferably 70 to 80% by weight, of comonomer, based on all comonomers, is selected as concentration of the comonomer or comonomers at the start of the copolymerization according to the invention. The copolymerization according to the invention can also be carried out as bulk polymerization, i.e. without the addition of solvents.

In one embodiment of the present invention, the copolymerization according to the invention is carried out as emulsion polymerization.

The copolymerization according to the invention can be carried out as a continuous method, as a semicontinuous method or in the form of a batch copolymerization.

In one embodiment of the present invention, the (co)polymerization according to the invention is carried out at temperatures in the range from 60 to 90° C.

Performing the method according to the invention gives copolymer according to the invention.

The present invention further provides compounds of the general formula IV a

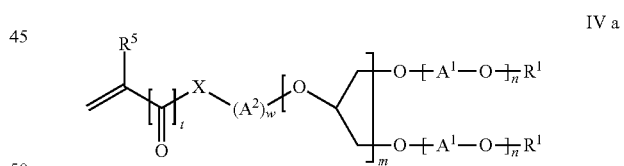

in which the variables are as defined above:
$R^1$ is different or preferably identical and selected from hydrogen or preferably $C_6$-$C_{30}$-aryl, preferably $C_6$-$C_{14}$-aryl, in particular phenyl; $C_7$-$C_{30}$-aralkyl, preferably benzyl; $C_3$-$C_{10}$-cycloalkyl, preferably cyclopentyl or cyclohexyl, and in particular $C_1$-$C_{30}$-alkyl, preferably $C_1$-$C_{20}$-alkyl.
$A^1$ is different or preferably identical and selected from $C_6$-$C_{10}$-arylene, preferably phenylene, $C_7$-$C_{10}$-aralkylene, such as, for example —CH($C_6H_5$)— or —$CH_2$—CH ($C_6H_5$)—, and in particular from $C_2$-$C_{10}$-alkylene, substituted or preferably unsubstituted, preferably —$CH_2$—$CH_2$—, —CH($CH_3$)—$CH_2$—, —$CH_2$—CH($CH_3$)—, very particularly preferably —$CH_2$—$CH_2$—,
n is different or identical and selected from zero to 200, preferably 1 to 150, particularly preferably 5 to 50, m is selected from 1 to 6, preferably to 4, particularly preferably to 2, $R^5$ is selected from hydrogen and methyl, t is selected from zero and one, w is selected from zero and one, $A^2$ is selected from $C_1$-$C_{50}$-alkylene, substituted or preferably unsubstituted, where one or more nonadjacent $CH_2$ groups may be replaced by oxygen. Examples of particularly suitable groups $A^2$ are $C_2$-$C_{10}$-alkylene, preferably —$CH_2$—$CH_2$—, —$CH(CH_3)$—$CH_2$—, —$CH_2$—$CH(CH_3)$—, particularly preferably —$CH_2$—$CH_2$—, furthermore —$CH_2$—$CH_2$—O—, —$CH(CH_3)$—$CH_2$—O—, —$CH_2$—$CH(CH_3)$—O—, —[$CH_2$—$CH_2$—O]$_y$—, —[$CH(CH_3)$—$CH_2$—O]$_y$—, —[$CH_2$—$CH(CH_3)$—O—]$_y$, where y is an integer in the range from 2 to 20, preferably 2 to 15 and in particular 3 to 10.

The present invention further provides compounds of the general formula IV b

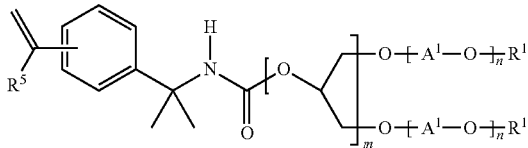

IV b

Here, the variables are as defined above:

$R^1$ is different or preferably identical and selected from hydrogen or preferably $C_6$-$C_{30}$-aryl, preferably $C_6$-$C_{14}$-aryl, in particular phenyl; $C_7$-$C_{30}$-aralkyl, preferably benzyl; $C_3$-$C_{10}$-cycloalkyl, preferably cyclopentyl or cyclohexyl, and in particular $C_1$-$C_{30}$-alkyl, preferably $C_1$-$C_{20}$-alkyl;

$A^1$ is different or preferably identical and selected from $C_6$-$C_{10}$-arylene, preferably phenylene, $C_7$-$C_{10}$-aralkylene, such as, for example —$CH(C_6H_5)$— or —$CH_2$—$CH(C_6H_5)$—, and in particular from $C_2$-$C_{10}$-alkylene, substituted or preferably unsubstituted, preferably —$CH_2$—$CH_2$—, —$CH(CH_3)$—$CH_2$—, —$CH_2$—$CH(CH_3)$—, very particularly preferably —$CH_2$—$CH_2$—, n is different or identical and selected from zero to 200, preferably 1 to 150, particularly preferably 5 to 50, m is selected from 1 to 6, preferably to 5, particularly preferably 2 to 4, $R^5$ is selected from hydrogen and methyl.

Compounds according to the invention of the general formula IV a and IV b are very highly suitable, for example, for preparing compounds (B) according to the invention. Their preparation takes place, for example, by the method described above.

The invention is illustrated by working examples.

General remarks: the synthesis of the compounds of the formula VI and IV was carried out in solvents which had been dried by standard methods.

Determination of the molecular weights carried out by GPC in DMAC (N,N-dimethylacetamide as solvent), Standard: PMMA.

Dioxane is always understood as meaning 1,4-dioxane, unless stated otherwise.

The (co)polymerization was carried out under a protective gas atmosphere (dried nitrogen).

Data in % are always % by weight, unless expressly stated otherwise.

I. PREPARATION OF COMPOUNDS OF THE GENERAL FORMULA VI

I.1 Preparation of Compound VI.1 According to the Invention

A solution of 400 g (0.29 mol) of polyethylene glycol monostearyl ether, $CH_3$—$(CH_2)_{17}$—O—$(CH_2CH_2$—O$)_{25}$H, in 1150 ml of dioxane was initially introduced in a 2 liter flask fitted with dropping funnel, magnetic stirrer and reflux condenser. With stirring, 25 g of KOH pellets were added. The mixture was heated 105° C. and then 14 g (0.15 mol) of epichlorohydrin, dissolved in 50 ml of dioxane, was added dropwise over a period of 15 minutes. The mixture, which was red-brown meanwhile, was stirred over a period of 15 hours at 105° C. and then cooled to room temperature. The resulting precipitate was filtered off and the dioxane was distilled off at 30 mbar. This gave compound VI.1 according to the invention, a viscose pale brown oil which was characterized by MS (Maldi TOF) and by GPC. $M_n$: 3200 g/mol, $M_w$: 4200 g/mol.

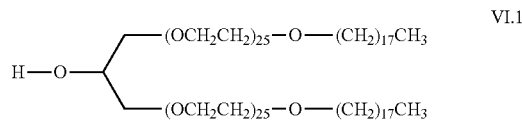

VI.1 m = 1

I.2 Preparation of Compound VI.2 According to the Invention

A solution of 400 g (0.53 mol) of polyethylene glycol monomethyl ether ($M_w$=750 g/mol, n=16) in 1150 ml of dioxane was initially introduced in a 2 liter flask fitted with dropping funnel, magnetic stirrer and reflux condenser. With stirring, 30 g of KOH pellets were added. The mixture was heated to 105° C. and then 25 g (0.26 mol) of epichlorohydrin dissolved in 50 ml of dioxane, was added dropwise over a period of 30 minutes. The mixture obtainable in this way was stirred over a period of 15 hours at 105° C. and then cooled to room temperature. The resulting precipitate was filtered off and the dioxane was distilled off at 30 mbar. This gave compound VI.2 according to the invention, a viscose yellowish oil, which was characterized by MS (Maldi TOF) and by GPC. $M_n$=1800 g/mol, $M_w$=2400 g/mol.

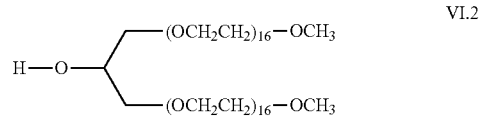

VI.2 m = 1

I.3 Preparation of Compound VI.3 According to the Invention

A solution of 365 g (1.04 mol) of H—$(OCH_2CH_2)_7$—O-n-$C_{12}H_{25}$ ($M_w$=490 g/mol, n=7) in 1600 ml of dioxane was initially introduced in a 2 liter flask fitted with dropping funnel, magnetic stirrer and reflux condenser. With stirring, 67 g of KOH pellets were added. The mixture was heated to 105° C. and then 35 g (0.37 mol) of epichlorohydrin, dissolved in 100 ml of dioxane were added dropwise over a period of 30 minutes. The mixture obtainable in this way was stirred over a period of 15 hours at 105° C. and then cooled to room temperature. The resulting precipitate was filtered off and the dioxane was distilled off at 30 mbar. This gave compound VI.3 according to the invention, a yellowish oil, which was characterized by MS (Maldi TOF) and by GPC. $M_n$=1470 g/mol, $M_w$=1940 g/mol.

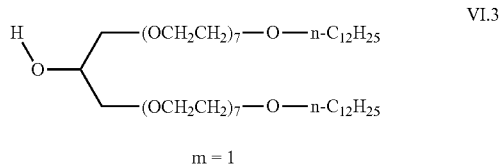

I.4 Preparation of Compound VI.4 According to the Invention

A solution of 700 g (0.93 mol) of H—(OCH$_2$CH$_2$)$_{16}$—OCH$_3$ ($M_w$=750 g/mol, n=16) in 1600 ml of dioxane was initially introduced in a 4 liter flask fitted with dropping funnel, magnetic stirrer and reflux condenser. With stirring, 224 g of KOH pellets were added. The mixture was heated to 105° C. and then 43 g (0.45 mol) of epichlorohydrin, dissolved in 175 ml of dioxane, were added dropwise over a period of 30 minutes. The mixture obtainable in this way was stirred over a period of 2 hours and then a further 21 g (0.23 mol) of epichlorohydrin in 100 ml of dioxane were added dropwise over a period of 30 minutes. The mixture obtainable in this way was stirred over a period of 2 hours and then a further 10.8 g (0.115 mol) of epichlorohydrin in 50 ml of dioxane were added dropwise over a period of 15 minutes. The mixture was stirred for 15 hours at 105° C. and then cooled to room temperature. The resulting precipitate was filtered off and the dioxane was distilled off at 30 mbar. This gave compound VI.4 according to the invention, a yellowish oil, which was characterized by MS (Maldi TOF) and by GPC. $M_n$=2400 g/mol, $M_w$=3100 g/mol.

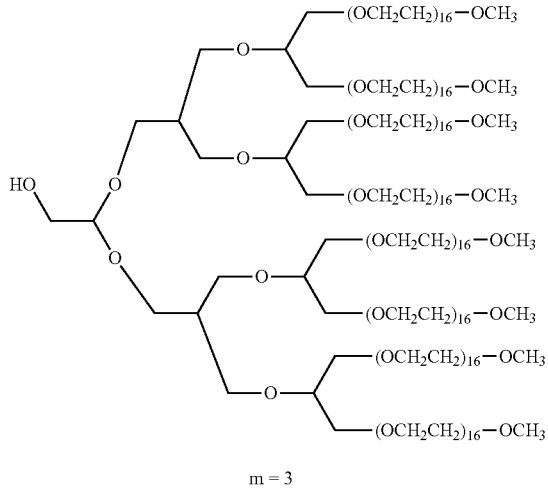

II. PREPARATION OF COMPOUNDS ACCORDING TO THE INVENTION OF THE GENERAL FORMULA IV

II.1 Preparation of Compound IV.1 According to the Invention from Compound VI.1 According to the Invention A solution of 200 g of compound VI.1 in 800 ml of THF was initially introduced in a 2000 ml flask equipped with dropping funnel and magnetic stirrer. The mixture was stirred for 20 minutes at room temperature and 50 mg of para-N,N-dimethylaminopyridine were added. Then, over a period of 15 minutes, a solution of 15.5 g of methacrylic anhydride, dissolved in 50 ml of THF, was added dropwise. The formation of a small amount of precipitate was observed. The mixture was stirred for a further 3 hours at room temperature, the precipitate was separated off by filtration and then the THF was distilled off at room temperature and reduced pressure. This gave compound IV.1 according to the invention as brown oil, which was characterized by MALDI-TOF and GPC.

II.2 Preparation of Compound IV.2 According to the Invention from Compound VI.2 According to the Invention A solution of 200 g of compound VI.2 in 800 ml of THF was initially introduced in a 2 l flask which was equipped with dropping funnel and magnetic stirrer. The mixture was stirred for 20 minutes at room temperature and 50 mg of para-N,N-dimethylaminopyridine were added. Then, over a period of 15 minutes, a solution of 9 g of methacrylic anhydride, dissolved in 50 ml of THF, was added dropwise. The formation of a small amount of precipitate was observed. The mixture was stirred for a further 3 hours at room temperature, the precipitate was separated off by filtration and then the THF was distilled off at room temperature and reduced pressure. This gave compound IV.2 according to the invention as a brown solid.

II.3 Preparation of Compound IV.3 According to the Invention from Compound VI.3 According to the Invention A solution of 200 g of compound VI.3 in 600 ml of THF was initially introduced in a 1 l flask which was equipped with dropping funnel and magnetic stirrer. The mixture was stirred for 20 minutes at room temperature and 50 mg of para-N,N-dimethylaminopyridine were added. Then, over a period of 20 minutes, a solution of 19 g of methacrylic anhydride, dissolved in 50 ml of THF, was added dropwise. The mixture was stirred for a further 3 hours at room temperature and filtered and then the THF was distilled off at room temperature and reduced pressure. This gave compound IV.3 according to the invention, which was characterized by MALDI-TOF.

II.4 Preparation of Compound IV.4 According to the Invention from Compound VI.4 According to the Invention 1000 g of compound VIA according to the invention and 10 g of KOH were initially introduced in a 2.5 l autoclave, rendered inert with nitrogen (2 bar) and then heated to 120° C. Acetylene was then injected to a pressure of 20 bar and the reaction mixture was stirred at 120° C. and 20 bar until a total of 85 l of acetylene had been absorbed. The mixture was then cooled to room temperature and decompressed and the residue, after heating at 60° C. for 3 h with stirring, was degassed and then removed from the autoclave. Compound IV.4 was characterized by $^1$H NMR spectroscopy.

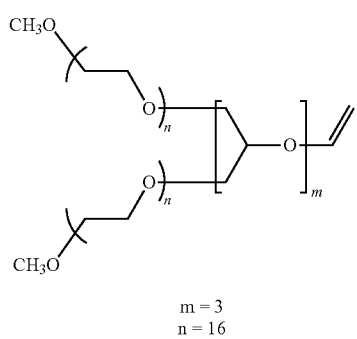

IV.4 m = 3
n = 16

III. PREPARATION OF COLPOLYMERS ACCORDING TO THE INVENTION

General Remarks:

Dispersed copolymers according to the invention were prepared from the compounds IV.1 to IV.3 according to the invention. For the application of these dispersed copolymers according to the invention in detergents and cleaners, and also for cosmetic articles, the invention is illustrated in more detail by the following application examples.

III.1 Preparation of a Copolymer According to the Invention (CP.1)

Emulsion E.3.1 is prepared, consisting of
220 g of completely demineralized water (demin. water)
137.3 g of methacrylic acid (A.1)
155.3 g of ethyl acrylate (C.1)
164.4 g of n-butyl acrylate (C.2)
12.5 g of compound IV.1 according to the invention (B.1)
12.32 g of a 28% by weight aqueous solution of lauryl ether sulfate as emulsifier Emul.1.
8.63 g of a 0.4% aqueous ascorbic acid solution In a stirred apparatus, consisting of a 2 liter HWS vessel with anchor stirrer (175 rpm), reflux condenser, internal thermosensor and metering station, 675.9 g of demineralized water (demin. water), 0.2 g of a 4% by weight [FeK$_2$(EDTA)] solution (EDTA=ethylendiamine tetraacetate) and 12.3 g of a 28% by weight aqueous solution of lauryl ether sulfate) were mixed together as initial charge. The mixture was heated to 75° C. 9.2 g of a 1% by weight aqueous hydrogen peroxide solution were then added. Then, with further stirring at 75° C., 50% of the emulsion E.3.1 were metered in. The reaction mixture was then cooled to 65° C. At 65° C., the remaining emulsion E.3.1 was metered in. The mixture was stirred at 65° C. over a period of 23 minutes. 6.6 g of a 7% by weight aqueous Na$_2$S$_2$O$_8$ solution and 86.2 g of a 0.4% strength ascorbic acid solution were then metered in. The reaction mixture was then cooled to room temperature. This gave an aqueous dispersion of copolymer CP.1 according to the invention which had a solids content of 31%.

III.2 Preparation of the Copolymers CP.2 to CP.10 According to the Invention The data relating to copolymers CP.2 to CP.10 according to the invention can be found in Table 1.

To prepare CP.2 to CP.10, the procedure was as under III.1, except the fractions of comonomers were varied. Furthermore, the type and amount of emulsifier as in Table 1 was used.

Emulsifier Emul.2 is to be understood as meaning sulfosuccinic acid di-2-ethylhexyl ester Na salt.

The quantitative data for the feed materials are given in parts by weight per 100 parts of reactive monomer (parts per hundred monomers; pphm). For characterizing the dispersion, the following values were measured:

Solids content, "solids": the dispersion in question was dried at 140° C. for 30 min and the solids content was determined in percent from the ratio of dry residue to initial weight.

Particle diameter: the dispersion in question was diluted with water to 0.01% and the particle diameter was measured by means of light scattering in the "High Performance Particle Sizer 5001" (HPPS) from Malvern Instruments.

LT value: the dispersion in question was diluted with water to 0.01% and the light transparency (LT) of the dispersion was measured optically in the Hach DR/2010 compared to pure water as a measure of the particle diameter.

TABLE 1

Synthesis, composition and properties of copolymers CP.1 to CP.7 according to the invention

|      | (A.1) | (B)        | (C.1)  | (C.2)  | Emulsifier    | Solids        | Ø    | LT    |
|------|-------|------------|--------|--------|---------------|---------------|------|-------|
|      | [pphm in each case] | | | | | [% by weight] | [nm] | value |
| CP.1 | 29.25 | 1.25 (IV.1) | 35.75 | 33.75 | 1.5 (Emul. 1) | 30.6 | 60 | 98 |
| CP.2 | 29.25 | 0.75 (IV.2) | 36.06 | 33.94 | 1.5 (Emul. 1) | 30.7 | 95 | 98 |
| CP.3 | 28.2  | 2.5 (IV.1)  | 34.67 | 34.67 | 3.0 (Emul. 2) | 31.3 | 82 | 97 |
| CP.4 | 29.25 | 1.25 (IV.1) | 35.74 | 33.75 | 3.0 (Emul. 2) | 30.7 | 68 | 95 |
| CP.5 | 29.25 | 1.25 (IV.1) | 35.74 | 33.75 | 1.5 (Emul. 2) | 31.1 | 93 | 95 |
| CP.6 | 28.8  | 1.25 (IV.2) | 35.0  | 35.0  | 3.0 (Emul. 2) | 31.2 | 84 | 96 |
| CP.7 | 30.0  | 2.5 (IV.1)  | 33.75 | 33.75 | —             | 30.3 | 64 | 98 |

IV. TESTING COPOLYMERS ACCORDING TO THE INVENTION IN LIQUID DETERGENTS

For the application testing, copolymers according to the invention were stirred into stock formulations for liquid detergents as in Table 2 and the thickening effect was tested. The stock formulations were selected from the following stock formulations.

Stock Formulation 1:
The following were mixed together:
13.0 g of para-n-$C_{10}$-$C_{13}$-alkyl-$C_6H_4$—$SO_3H$,
7.5 g of $CH_3(CH_2)_{11}$—(O—$CH_2CH_2)_7$—OH
8.5 g of coconut fatty acid (fatty acid mixture)
4.4 g of KOH
3.0 g of sodium citrate dihydrate
8.0 g of 1,2-propylene glycol
2.0 g of ethanol
and topped up to 90 g with water.

Stock Formulation 2:
The following were mixed together:
17.9 g of para-n-$C_{10}$-$C_{13}$-alkyl-$C_6H_4$—$SO_3H$
20.0 g of $CH_3(CH_2)_{11}$—(O—$CH_2CH_2)_7$—OH
8.5 g of coconut fatty acid (fatty acid mixture)
5.0 g of KOH
3.0 g sodium citrate dihydrate
8.0 g of 1,2-propylene glycol
2.0 g of ethanol
and topped up to 90 g with water.

Stock Formulation 3:
The following were mixed together:
13.4 g of para-n-$C_{10}$-$C_{13}$-alkyl-$C_6H_4$—$SO_3H$
10.0 g $CH_3(CH_2)_{11}$—(O—$CH_2CH_2)_7$—OH
8.5 g of coconut fatty acid (fatty acid mixture)
4.4 g of KOH
3.0 g of sodium citrate dihydrate
8.0 g of 1,2-propylene glycol
2.0 g of ethanol
and topped up to 90 g with water.

General Procedure:
90 g of stock formulation, aqueous dispersion of copolymer according to the invention and water were mixed so that liquid detergents LD.1 to LD.7 according to the invention as in Table 2 resulted. The liquid detergents according to the invention were left to rest at room temperature for at least 5 hours and then the application properties were tested. The results are summarized in Table 2.

As reference formulation, in each case the stock formulation in question was diluted to 100 g with water.

TABLE 2

Application testing of liquid detergents according to the invention

| LD | Solids [%] | Stock formulation | CP [g/100 g] | Viscosity [mPa · s] |
|---|---|---|---|---|
| C-LD.0 | 31.0 | No. 1 | — | 78 |
| LD.1 | 30.6 | No. 1 | 0.8 (CP.1) | 540 |
| LD.2 | 30.7 | No. 1 | 0.8 (CP.2) | 570 |
| LD.3 | 31.3 | No. 1 | 0.8 (CP.3) | 567 |
| LD.4 | 30.7 | No. 1 | 0.8 (CP.4) | 633 |
| LD.5 | 31.1 | No. 1 | 0.8 (CP.5) | 579 |
| LD.6 | 31.2 | No. 1 | 0.8 (CP.6) | 564 |
| LD.7 | 31.3 | No. 1 | 1.4 (CP.4) | 874 |
| LD.8 | 30.7 | No. 1 | 1.4 (CP.5) | 1123 |
| LD.9 | 31.1 | No. 1 | 1.4 (CP.6) | 1083 |
| LD.10 | 30.3 | No. 2 | 1.5 (CP.7) | 927 |
| C-LD.11 | 31.1 | No. 2 | — | 76 |
| LD.12 | 30.3 | No. 3 | 1.5 (CP.7) | 902 |
| C-LD.13 | 29.9 | No. 3 | — | 72 |

The viscosity was measured taking into consideration the procedures in accordance with DIN 51550, DIN 53018, DIN 53019 using the Brookfield viscometer model RV-03 at a rotational speed of 20 revolutions per minute with spindle No. 62 at 20° C. The viscosity of the unthickened reference formulations can be found in Table 1, comparative examples 1 to 3.

To quantify the transparency of the liquid detergent according to the invention, the transmission in % was measured at 440 nm at 23° C. using a LICO 200 from Dr. Lange. The transmission of the unthickened reference formulation and of the liquid detergents according to the invention was in the same range between 97 and 100%. The addition of copolymers according to the invention caused no clouding in the liquid detergent according to the invention.

The invention claimed is:

1. A copolymer comprising, as comonomers in copolymerized form:
   (A) at least one ethylenically unsaturated mono- or dicarboxylic acid;
   (B) at least one ethylenically unsaturated compound which has at least one structural unit of the general formula (I) per molecule:

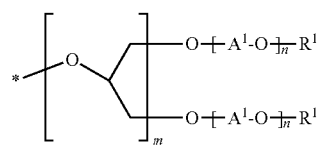

wherein:
each $R^1$ is different or identical and represents a hydrogen atom, a $C_1$-$C_{30}$-alkyl, a $C_3$-$C_{10}$-cycloalkyl, a $C_6$-$C_{30}$-aryl or a $C_7$-$C_{30}$-aralkyl,
each $A^1$ is different or identical and represents a $C_2$-$C_{10}$-alkylene, a $C_6$-$C_{10}$-arylene or a $C_7$-$C_{10}$-aralkylene,
each m is different or identical and represents an integer from 2 to 6,
each n is different or identical and represents an integer from zero to 200; and
(C) at least one further comonomer.

2. The copolymer according to claim 1, which has at least one structural unit of the general formula (II)

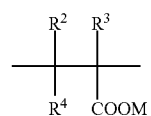

wherein:
each $R^2$ and $R^3$ is identical or different and represents a $C_1$-$C_6$-alkyl or a hydrogen atom,
each $R^4$ represents a $C_1$-$C_6$-alkyl, a COOM or a hydrogen atom, and
each M represents a substituted or unsubstituted ammonium group, a hydrogen atom, or a metal cation.

3. The copolymer according to claim 1, wherein compound (B) has a molecular weight $M_w$ in the range from 200 to 100 000 g/mol.

4. The copolymer according to claim 1, wherein compound (B) has a K value in accordance with Fikentscher in the range from 8 to 40, measured in water/THF mixtures.

5. The copolymer according to claim 2, wherein the molar ratio of structural units of the formula I to structural units of the formula II is in the range from 0.01 to 10.

6. The copolymer according to claim 1, wherein at least one structural unit of the general formula I is bonded to the basic backbone of said copolymer via a group of the formula III a

or III b

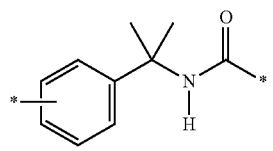

wherein:
X represents a single bond, an oxygen atom, or N—H group,
t represents zero or one,
w represents zero or one,
$A^2$ represents a substituted or unsubstituted $C_1$-$C_{50}$-alkylene, where one or more nonadjacent $CH_2$ groups thereof may be replaced by an oxygen atom.

7. A detergent or cleaner or cosmetic preparation comprising at least one copolymer according to claim 1.

8. A compound (B), which comprises, in copolymerized form, at least one comonomer of the general formula IV a or IV b,

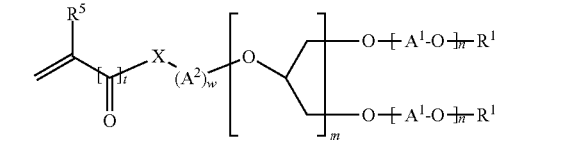

wherein:
each $R^1$ is different or identical and represents a hydrogen atom, a $C_1$-$C_{30}$-alkyl, a $C_3$-$C_{10}$-cycloalkyl, a $C_6$-$C_{30}$-aryl or a $C_7$-$C_{30}$-aralkyl,
each $A^1$ is different or identical and represents a $C_2$-$C_{10}$-alkylene, a $C_6$-$C_{10}$-arylene or a $C_7$-$C_{10}$-aralkylene,
m is different or identical and represents an integer from 2 to 6,
n is different or identical and represents an integer from zero to 200,
$R^5$ represents a hydrogen atom or a methyl group,
t represents zero and one,
w represents zero and one,
X is represents a single bond, an oxygen atom, or a N—H group,
$A^2$ represents a substituted or unsubstituted $C_1$-$C_{50}$-alkylene, where one or more nonadjacent $CH_2$ groups may be replaced by an oxygen atom.

9. A method of preparing (co)polymers according to claim 1, comprising free-radically copolymerizing (A) at least one ethylenically unsaturated mono- or dicarboxylic acid, (B) at least one (co)monomer of the general formula IV a or IV b

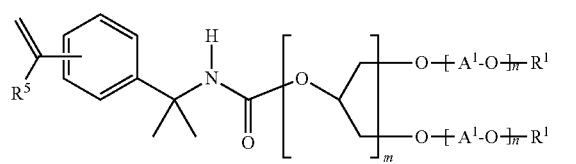

and (C) at least one comonomer of the general formula V a to V c $$\begin{array}{c} R^4 \diagdown \quad \diagup COOM \\ \diagup \quad \diagdown \\ R^2 \quad R^3 \end{array} \quad V\,a$$

$$\begin{array}{c} R^2 \diagdown \quad \diagup COOM \\ \diagup \quad \diagdown \\ R^4 \quad R^3 \end{array} \quad V\,b$$

$$V\,c$$

V b
to obtain the copolymer,
wherein:
each $R^2$ and $R^3$ is identical or different and represents a $C_1$-$C_6$-alkyl or a hydrogen atom,
$R^4$ represents a $C_1$-$C_6$-alkyl, a COOM group, or a hydrogen atom,
M represents a substituted or unsubstituted ammonium group, a hydrogen atom or a metal cation,
$R^5$ represents a hydrogen atom or a methyl group,
each $R^1$ is different or identical and represents a hydrogen atom, a $C_1$-$C_{30}$-alkyl, a $C_3$-$C_{10}$-cycloalkyl, a $C_6$-$C_{30}$-aryl or a $C_7$-$C_{30}$-aralkyl,
each $A^1$ is different or identical and represents $C_2$-$C_{10}$-alkylene, a $C_6$-$C_{10}$-arylene or a $C_7$-$C_{10}$-aralkylene,
each m is different or identical and represents an integer from 2 to 6,
each n is different or identical and represents an integer from zero to 200
t represents zero or one,
w represents zero or one, X represents a single bond, an oxygen atom, or a N—H group, $A^2$ represents a substituted or unsubstituted $C_1$-$C_{50}$-alkylene, where one or more nonadjacent $C_{1-2}$ groups may be replaced by an oxygen atom.

10. The copolymer according to claim 1, wherein, per molecule, compound (B) has from one to ten of structural units represented by formula (I).

11. The copolymer according to claim 1, wherein each $R^1$, different or identical, represents a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1,2-dimethylpropyl group, an isoamyl group, a n-hexyl group, an isohexyl group, or a sec-hexyl group.

12. The copolymer according to claim 1, wherein each n is different or identical and selected from 1 to 150.

13. The copolymer according to claim 1, wherein each n is different or identical and selected from 5 to 50.

14. The copolymer according to claim 1, wherein said at least one further comonomer comprises at least one member selected from the group consisting of (meth)acrylic acid, methyl (meth)acrylate, ethyl (meth)acrylate, n-butyl (meth)acrylate, 2-ethylhexyl (meth)acrylate, vinyl acetate, styrene, α-methylstyrene, a $C_{12}$-$C_{20}$-α-olefin, vinyl chloride, acrylonitrile, and N-vinylpyrrolidone.

* * * * *

UNITED STATES PATENT AND TRADEMARK OFFICE
CERTIFICATE OF CORRECTION

PATENT NO. : 8,492,497 B2
APPLICATION NO. : 12/834310
DATED : July 23, 2013
INVENTOR(S) : Rabie Al-Hellani et al.

It is certified that error appears in the above-identified patent and that said Letters Patent is hereby corrected as shown below:

On the title page, Item (75), the 6th inventor's name is incorrect. Item (75) should read:

--(75) Inventors: Rabie Al-Hellani, Ludwigshafen (DE);
Bernd Bruchmann, Freinsheim (DE);
Daniel Schoenfelder, Brussels (BE);
Anna Cristadoro, Heppenheim (DE);
Reinhold J Leyrer, Dannstadt-Schauernheim (DE);
Christofer Arisandy, Ilvesheim (DE)--

Signed and Sealed this
Twenty-fourth Day of September, 2013

Teresa Stanek Rea
*Deputy Director of the United States Patent and Trademark Office*